(12) United States Patent
Prabhakarpandian et al.

(10) Patent No.: US 9,784,727 B2
(45) Date of Patent: Oct. 10, 2017

(54) SYNTHETIC MICROFLUIDIC SYSTEMS FOR WOUND HEALING

(71) Applicant: CFD Research Corporation, Huntsville, AL (US)

(72) Inventors: Balabhaskar Prabhakarpandian, Madison, AL (US); Kapil Pant, Madison, AL (US)

(73) Assignee: CFD Research Corporation, Huntsville, AL (US)

( * ) Notice: Subject to any disclaimer, the term of this patent is extended or adjusted under 35 U.S.C. 154(b) by 0 days.

(21) Appl. No.: 15/041,963

(22) Filed: Feb. 11, 2016

(65) Prior Publication Data

US 2016/0161469 A1    Jun. 9, 2016

Related U.S. Application Data

(62) Division of application No. 14/202,721, filed on Mar. 10, 2014, now Pat. No. 9,291,614.

(60) Provisional application No. 61/775,158, filed on Mar. 8, 2013.

(51) Int. Cl.
*C12Q 1/04* (2006.01)
*G01N 33/50* (2006.01)
*G01N 33/86* (2006.01)
*B01L 3/00* (2006.01)

(52) U.S. Cl.
CPC ..... *G01N 33/5029* (2013.01); *G01N 33/5005* (2013.01); *G01N 33/5011* (2013.01); *G01N 33/5061* (2013.01); *G01N 33/5088* (2013.01); *G01N 33/86* (2013.01); *B01L 3/5027* (2013.01); *G01N 2333/4703* (2013.01); *G01N 2333/70525* (2013.01)

(58) Field of Classification Search
CPC ..................................................... C12Q 1/04
See application file for complete search history.

(56) References Cited

U.S. PATENT DOCUMENTS

2004/0142411 A1    7/2004  Kirk et al.

*Primary Examiner* — Rosanne Kosson
(74) *Attorney, Agent, or Firm* — Maschoff Brennan

(57) ABSTRACT

A method of assaying wound healing can include: growing cells on the matrix in the first flow channel; introducing an agent that removes the matrix from the junction; introducing a matrix material into the second flow channel so as to form the second matrix in the second flow channel and junction; and detecting cellular migration into the junction onto the second matrix. The agent that removes the matrix can include a biomolecule or chemical agent. The method can include removing cells in the matrix in the junction before introducing the matrix material into the second flow channel. A bioactive agent can be introduced into the junction to determine if it modulates cellular migration and/or clot formation into the intersection openings of tissue and vascular channels.

19 Claims, 12 Drawing Sheets

SYNTHETIC MICROFLUIDIC SYSTEMS FOR WOUND HEALING

CROSS-REFERENCE

This patent application is a divisional of U.S. application Ser. No. 14/202,721 filed Mar. 10, 2014 that claims priority to U.S. Provisional Application No. 61/775,158 filed Mar. 8, 2013, which provisional application is incorporated herein by specific reference in its entirety.

BACKGROUND

Wounds and uncontrolled bleeding or hemorrhage remains the leading cause of preventable death following trauma. It is thought that about ⅓ of these deaths occur later than 10 minutes after injury, suggesting that effective and timely treatment can be useful in reducing deaths from wounds and hemorrhage. Treatments to control bleeding include fluid resuscitation, hemostatic dressings, pressure devices and drugs.

For treatment, it can be necessary to discover the source of bleeding. The source is either visible (e.g., arterial bleeding in limb trauma etc.) or invisible (e.g., internal bleeding). It can also be necessary to evaluate the amount of blood loss and potential for organ damage (e.g., cerebral coma after intracranial bleeding). A common feature observed during hemorrhagic shock is the drop in mean arterial pressure. The arterial pressure in case of Stage I and II has moderate drop but in Stage III and IV, the drop is significant and rapid treatment is necessary to control the bleeding and bring the body under hemostasis.

Hemorrhagic shock is typically treated by volume replacement, either with full blood or crystalloids followed by infusion of hemostatic agents to restore hemostasis. Three factors for normal hemostasis are: vessel wall, platelets, and plasma proteins (e.g., coagulation factors). Primary hemostasis occurs in seconds, as a platelet plug is formed. There are four steps of primary hemostasis: platelet activation, adhesion, degranulation and aggregation. During secondary hemostasis, coagulation factors of internal and external cascade are activated and fibrin is formed from fibrinogen.

However, volume replacement therapy can cause blood to lose its ability to clot resulting in coagulopathy by altering the coagulation factors. Coagulopathy can be attributed to a combination of factors: (a) depletion and dilution of coagulation factors and platelets, (b) metabolic acidosis, and (c) hypothermia. Depletion and dilution of coagulation factors and platelets can be due to the transfusion of crystalloid solutions, the body's rapid consumption of factors and platelets as it tries hard to achieve hemostasis and intravascular coagulation. In addition, metabolic derangements and hypothermia have been focused on as two variables that play a major role in maintaining hemostasis following bleeding. It has been observed that temperature drop from 37° C. to 33° C. drastically reduced the ability of platelets to form clots. Small changes in pH also reduces the activity of various enzymes involved in the coagulation process For example, a pH decrease from 7.4 to 7.0 has been found to reduce the activity of enzyme that activates thrombin by 70%. The replacement of missing factor(s) such as platelet and plasma proteins is needed to treat this condition. In addition, restoration of complete hemostasis in the body can require the introduction of hemostatic agents.

Current in vitro models for testing wound healing and hemostatic efficacy of a dressing or agents rely primarily on experiments performed in static environments of test tubes. However, results obtained from these simplified experiments are not predictive of animal or human vascular injury. This is due to the fact that in vivo conditions are significantly different than the experimental conditions in vitro. They fail to reproduce both the injury characteristics (e.g., wound size, dilution, pH/temperature change) and the variety of physiological (e.g., blood flow, platelet adhesion) and biological (e.g., endothelial response, coagulation pathway) mechanisms involved in wound healing and stopping hemorrhage. This leads to critical deficits in the understanding of the interplay and relative importance of these mechanisms in wound healing and restoring hemostasis. Therefore, there remains a need in the art for a better system and methodology for studying wound healing and hemostasis.

SUMMARY

In one embodiment, a method of assaying wound healing can include: providing a device having a first flow channel that intersects a second flow channel at a junction, the first flow channel having an internal surface that is coated with a matrix; growing cells on the matrix in the first flow channel; injuring and/or removing cells in the junction if cells are in the junction; and detecting cellular migration of the cells from the first flow channel into the junction. In one aspect, the provided device has the matrix in the junction, the method further comprising: removing the matrix from the junction before the detecting of cellular migration into the junction. In one aspect, the method can include: after the matrix is removed from the junction, introducing a second matrix into the junction; and detecting cellular migration of the cells from the first flow channel onto the second matrix in the junction. In one aspect, the method can include: introducing the second matrix into the second flow channel in order to introduce the second matrix into the junction.

In one embodiment, the method can include: introducing an agent that removes the matrix and/or cells from the junction. In one aspect, the method can include:
introducing an agent that removes the matrix includes an enzyme, biomolecule, or chemical.

In one embodiment, the method can include: removing cells in the matrix in the junction before introducing the second matrix into the second flow channel.

In one embodiment, the method can include: introducing a bioactive agent into the junction; and determining whether the bioactive agent modulates cellular migration into the junction In one embodiment, the method can include: detecting cellular migration of the cells from the first flow channel into the junction having a first matrix material; detecting cellular migration of the cells from the first flow channel into the junction having a different second matrix material; and comparing the first matrix material to the different second matrix material for cellular migration into the junction.

In one embodiment, the cells used in the methods are primary cells or cell lines.

In one embodiment, the method can include: providing a third flow channel that intersects a fourth flow channel at a second junction, the third flow channel having an internal surface that is coated with a second matrix that is different from a first matrix in the first junction; detecting cellular migration of the cells from the first flow channel onto the first matrix in the first junction; and detecting cellular migration of the cells from the third flow channel onto the second matrix in the second junction.

In one embodiment, the method can include: comparing the cellular migration onto the first matrix with the cellular migration onto the second matrix.

In one embodiment, the method can include: comparing a first matrix material to a different second matrix material for the cellular migration into the junction.

In one embodiment, the method can include using a device that comprises: the first flow channel having an first inlet and a first outlet; the second flow channel having a second inlet and second outlet and the junction with the first flow channel, the junction being between the first inlet, first outlet, second inlet, and second outlet; and the matrix coated on an internal surface of the first flow channel between the first inlet and junction and/or between the junction and first outlet. In one aspect, the method can include growing cells on the matrix in the first flow channel between the first inlet and junction and/or between the junction and first outlet and/or in the junction. In one aspect, the method can include growing cells on the matrix in the first flow channel; introducing an agent that removes the matrix and/or cells from the junction; introducing a matrix material into the second flow channel so as to form the second matrix in the second flow channel and junction; and detecting cellular migration into the junction onto the second matrix. In one aspect, the agent that removes the matrix includes an enzyme, biomolecule, or chemical. In one aspect, the method can include introducing a bioactive agent into the junction; and determining whether the bioactive agent modulates cellular migration into the junction. In one aspect, the method can include comparing a first matrix material to a different second matrix material for cellular migration into the junction. In one aspect, the cells are primary cells or cell lines.

BRIEF DESCRIPTION OF THE FIGURES

The foregoing and following information as well as other features of this disclosure can become more fully apparent from the following description and appended claims, taken in conjunction with the accompanying drawings. Understanding that these drawings depict only several embodiments in accordance with the disclosure and are, therefore, not to be considered limiting of its scope, the disclosure can be described with additional specificity and detail through use of the accompanying drawings, in which:

DETAILED DESCRIPTION

Figure 1A:
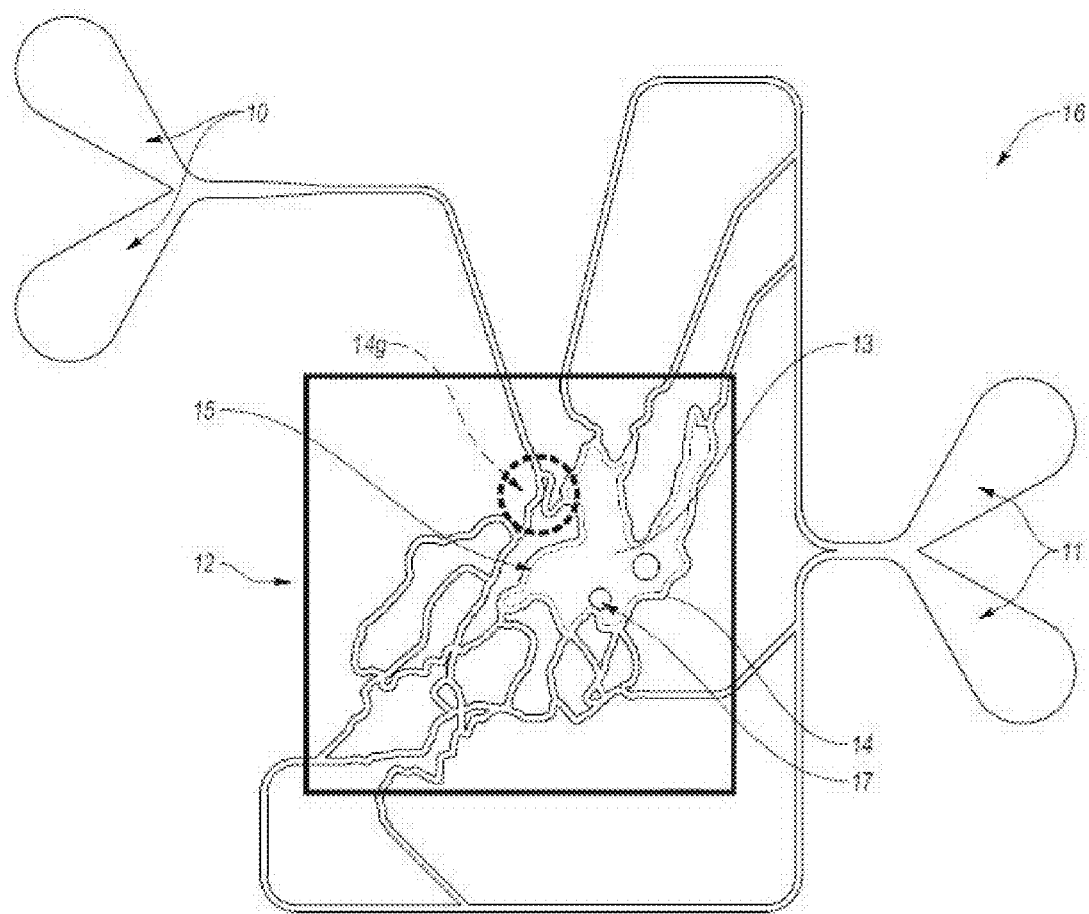
FIG. 1A illustrates an embodiment of a device having a plurality of tissue spaces connected by a plurality of fluid channels.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It can be readily understood that the aspects of the present disclosure, as generally described herein, and illustrated in the figures, can be arranged, substituted, combined, separated, and designed in a wide variety of different configurations, all of which are explicitly contemplated herein.

Generally, the present invention includes a device and methodology to study and characterize wound healing or hemostasis in idealized and physiologically realistic microenvironments. The device and methodologies can also be used to study targeted therapy for wound healing or hemostasis. The device is configured with an internal chamber and surrounding capillary channels to simulate the wound healing or hemostasis process. The device and methodologies allow for the study and visualization in real time of wound healing or hemostasis. The device and methodologies provide for an environment to facilitate studying the interplay between these cellular activities, and can provide for a platform for developing therapeutics for wound healing or hemostasis.

The device and methodology can be useful to study wound healing and hemostasis so that the information obtained can be used to reduce death, such as on the battlefield and in the hospital. The device can be used to study thrombotic potential, which is a major surgical concern and post-surgery complication. Hemostatic and anti-thrombotic drugs have proven useful in reducing mortality and morbidity, and the device can be used to test drugs and screen for new hemostatic and anti-thrombotic drugs as well as drugs that promote wound healing. The embodiments of the device can be used to test hemostatic agents in a manner that translates to relevant data when the agents are used in vivo. The device can be used with in vitro experiments conducted in complex fluid dynamic environments that simulate real physiological environments. Accordingly, the device can be used to reproduce the variety of physiological (e.g., blood flow, platelet adhesion) and biological (e.g., endothelial response, coagulation pathway) mechanisms involved in the complex processes of wound healing and/or hemostasis. This allows to an improved understanding of the interplay between and relative importance of each of these mechanisms in wound healing and hemostasis.

The present invention can include a microfluidic device in an idealized (e.g., linear and ordered, IMN) or realistic (e.g., non-linear and unordered, SMN) and assay that provides an accurate representation of wound healing, thrombosis, and hemostasis occurring under physiologic conditions. The device reproduces the morphological size, physiological blood flow, and cellular (e.g., biological) make-up of circulatory vessels. Various wound models can be readily created and investigated within the device of the present invention.

It can be used for conventional imaging-based end-point determinations or real time tracking, as well as medium to high-throughput screening.

Figures 1B, 1C:
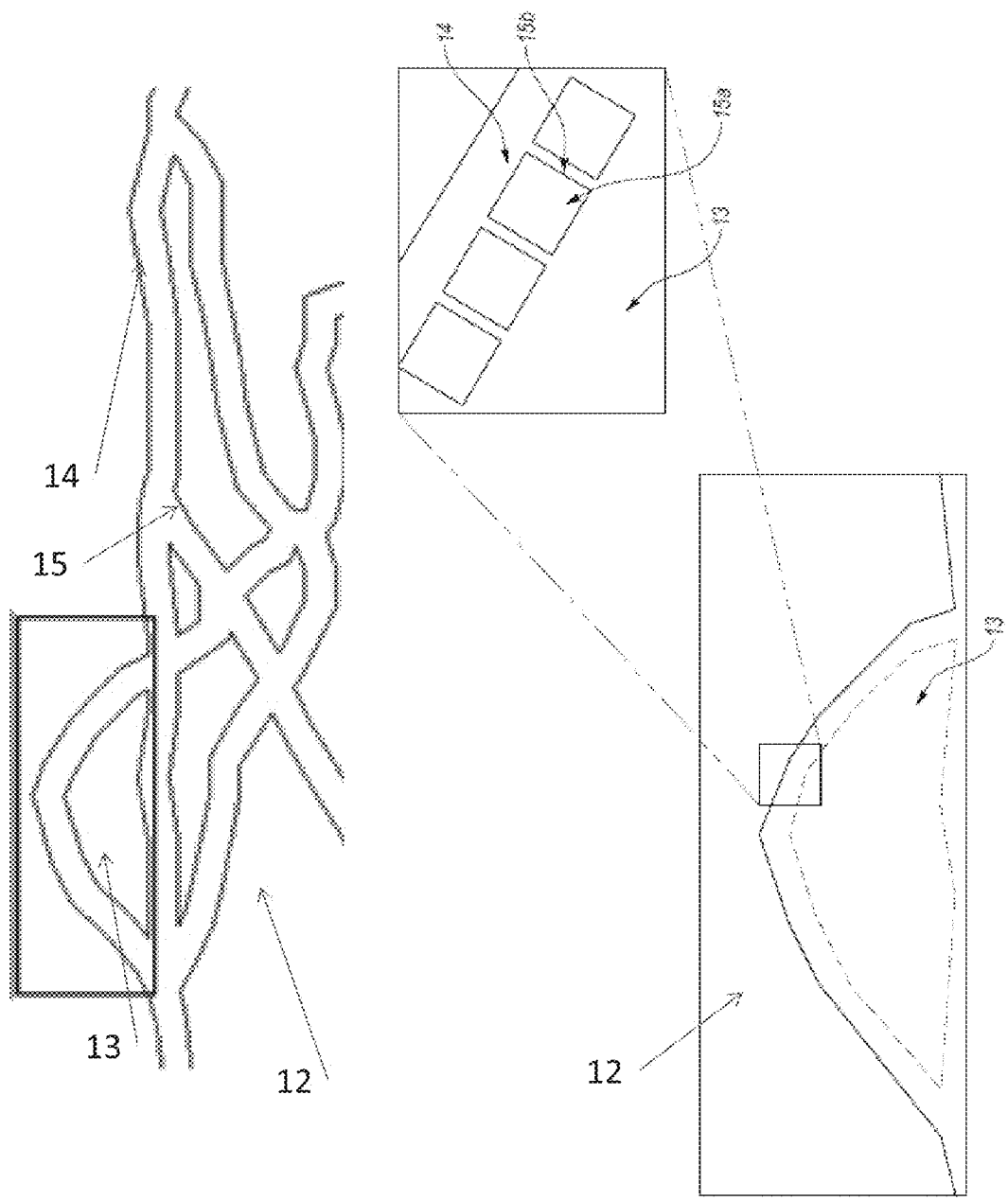
FIG. 1B illustrates a section of an embodiment of a device having a plurality of tissue spaces connected by a plurality of fluid channels.
FIG. 1C illustrates an embodiment of a porous wall that separates a tissue space and fluid channel of a device, where the wall fluidly couples the tissue space and fluid channel.
Figure 1D:
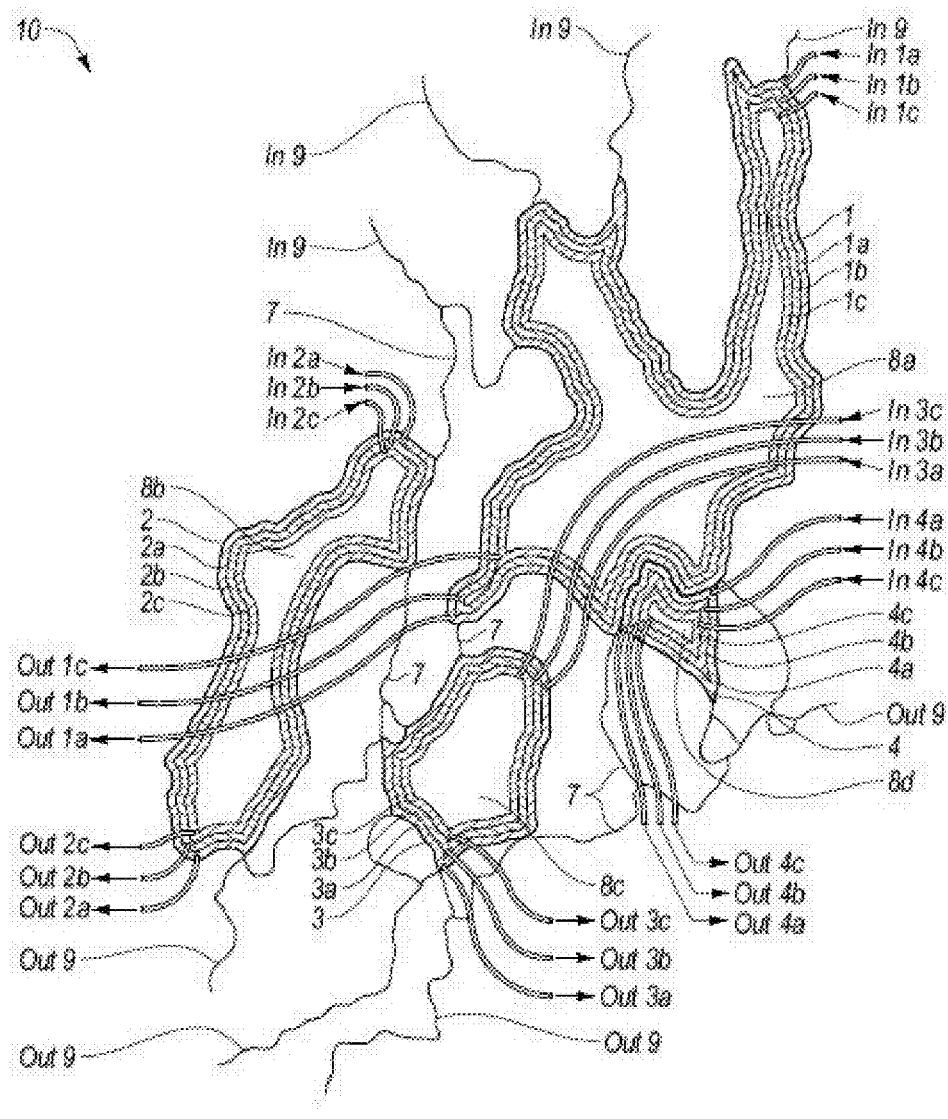
FIG. 1D illustrates an embodiment of a device having a plurality of tissue spaces connected by a plurality of fluid channels in a multi-channel orientation.

FIGS. 1A-1D illustrate an embodiment of a device 16 having a SMN 12 comprising an internal chamber (e.g., extravascular tissue space) surrounded by fluid microchannels (e.g., capillaries). An embodiment of a synthetic microvascular network (SMN) 12 can include realistic flow channels 14 with realistic features 14g and tissue spaces 13, as shown in FIGS. 1B-1D. The tissue space 13 and capillary network is irregular. Here, the wall of a flow channel (e.g., capillary channel) separating the flow channel lumen from the lumen of the tissue space 13 is shown in detail to show the pillars 15a and gaps 15b. In this embodiment, one wall of the nonlinear flow channel 14 is constructed such that portions of the wall contain gaps 15b located between portions of the wall, called pillars 15a (or posts, islands, etc.), which may be configured to provide gaps 15b of various selected sizes. For fabrication of the SMN 12 comprising the extravascular (extra-flow channel) tissue space 13, CAD drawings of a physiological network are modified to include gaps 15b with desired gaps or pores in the walls of the vessels. The patterns of these vessels include tissue sections comprising a portion of or the entire physiological tissue space. The lumens of the tissue spaces shown in FIG. 1B-1C may comprise posts, pillars, or other structures made of plastic substrate to facilitate the growth of adhesion-dependent cells. The SMN 12 can include inlet ports 10 and outlet ports 11. The tissue space may also include inlet/outlet ports 17. Any area surrounded by the flow channels 14 can be a tissue space 13.

The device can be made out of a clear plastic, such as PDMS, and modeled after vascular networks. The CAD drawings of the networks can be modified using AutoCAD LT to include 1-30 μm gaps at the walls of the channels and internal chambers. The size of the "structures" or "islands" (see FIG. 1B-1C) introduced in the walls as a result of these gaps is the single most critical element of the network topology modifications.

The modified network topology can be analyzed via high-fidelity computational modeling. The analyzed network can be fabricated using conventional soft lithography/replica casting techniques, such as those described herein.

The devices can include central chambers surrounded by at least two adjacent capillary channels. In view of the SMN of FIGS. 1A-1C, a corresponding SMN modeled after live physiology with at least two capillary channels would look like FIG. 1D. FIG. 1D illustrates an embodiment of SMN network having SMN fluid pathways and SMN multi-channeled cell culture constructs.

FIG. 1D illustrates a SMN 10 having one of more fluid inlets In 9 and one or more fluid outlets Out 9 with one or more multi-channel constructs 1, 2, 3, 4, each having a central chamber 8a, 8b, 8c, 8d (e.g., while four multi-channel constructs are shown, any integer can be used). The multi-channel constructs 1, 2, 3, 4 can be configured with inlets and outlets in accordance with any of the embodiments or figures described herein. Also, while shown to be SMN, the configuration can be an IMN. The SMN can be configured with any number of fluid pathways 7 linking the multi-channel constructs, which can be in any manner, and which SMN can be designed via simulation of real biological or artificial fluid pathways.

As shown, multi-channel construct 1 can include a central chamber 8a surrounded by an outer conduit layer 1a (e.g., outer capillary channel) with barrier layer channels 1b, 1c therebetween. The outer conduit layer 1a can be fluidly coupled with an inlet In 9 and an outlet Out 9. Also, the outer conduit layer 1a can include an inlet In 1a and an outlet Out 1a. The barrier layer channels 1b, 1c, can include inlets In 1b, In 1c and outlets Out 1b, Out 1c, respectively. While not shown, the central chamber 8a can include inlets or outlets, or it can receive content from the barrier layer channel 1c.

As shown, multi-channel construct 2 can include a central chamber 8b surrounded by an outer conduit layer 2a (e.g., capillary channel) with barrier layer channels 2b, 2c therebetween. The outer conduit layer 2a can be fluidly coupled with an inlet In 9 and an outlet Out 9. Also, the outer conduit layer 2a can include an inlet In 2a and an outlet Out 2a. The barrier layer channels 2b, 2c, can include inlets In 2b, In 2c and outlets Out 2b, Out 2c, respectively. While not shown, the central chamber 8b can include inlets or outlets, or it can receive content from the barrier layer channel 2c.

As shown, multi-channel construct 3 can include a central chamber 8c surrounded by an outer conduit layer 3a (e.g., outer capillary channel) with barrier layer channels 3b, 3c therebetween. The outer conduit layer 3a can be fluidly coupled with an inlet In 9 and an outlet Out 9. Also, the outer conduit layer 3a can include an inlet In 3a and an outlet Out 3a. The barrier layer channels 3b, 3c, can include inlets In 3b, In 3c and outlets Out 3b, Out 3c, respectively. While not shown, the central chamber 8a can include inlets or outlets, or it can receive content from the barrier layer channel 3c.

As shown, multi-channel construct 4 can include a central chamber 8d surrounded by an outer conduit layer 4a with barrier layer channels 4b, 4c therebetween. The outer conduit layer 4a can be fluidly coupled with an inlet In 9 and an outlet Out 9. Also, the outer conduit layer 4a can include an inlet In 4a and an outlet Out 4a. The barrier layer channels 4b, 4c, can include inlets In 4b, In 4c and outlets Out 4b, Out 4c, respectively. While not shown, the central chamber 8d can include inlets or outlets, or it can receive content from the barrier layer channel 4c. For example, a cancer cell can leave one chamber and travel through the fluid channels to a different chamber, which can be studied with the present invention.

Figure 10:
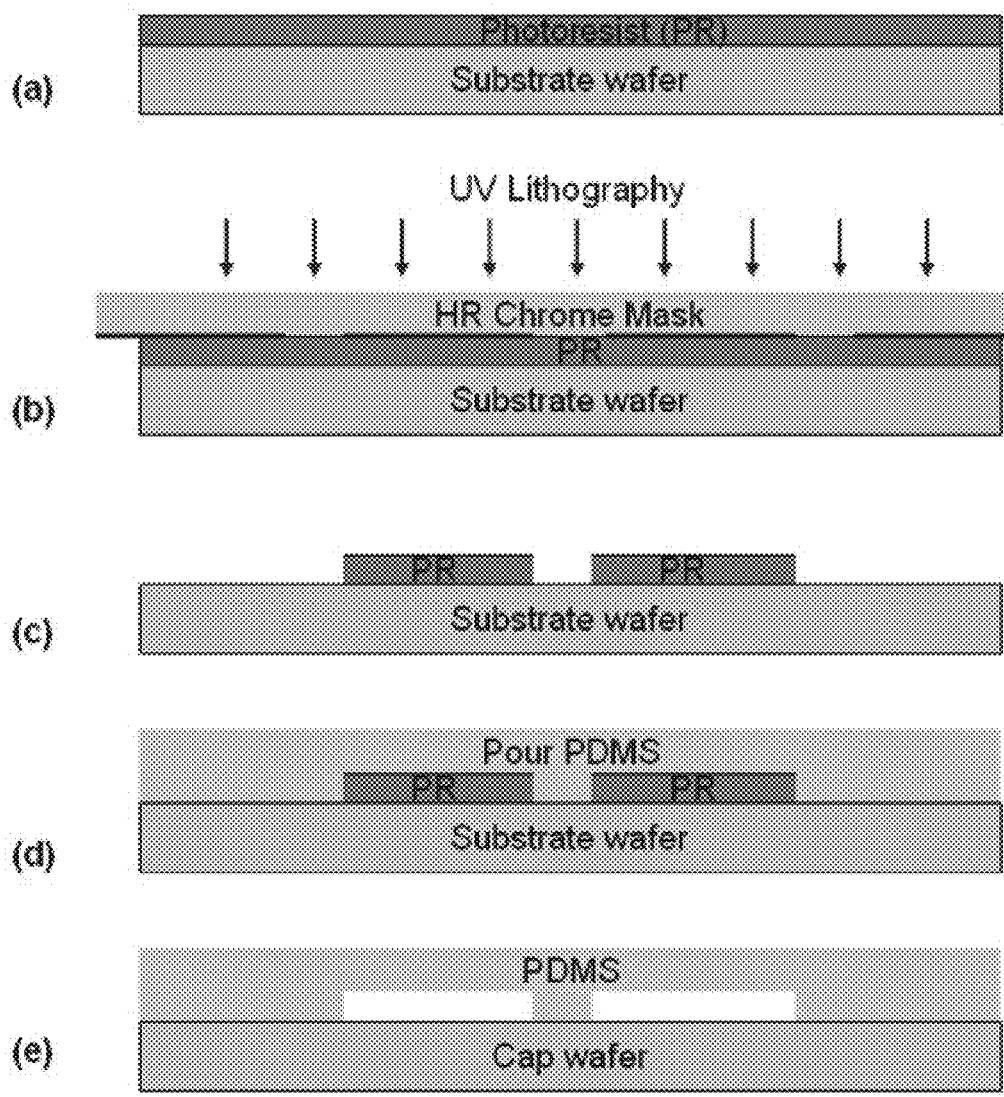
FIG. 10 illustrates a method of manufacturing a device of the invention.

The device can be fabricated with PDMS using conventional soft lithography (see FIG. 10). CAD drawings of the device can be developed to include post structures with gaps to act as paths for diffusion of fluid (e.g., nutrients or oxygen) into the central cell chamber. The CAD drawings can also be converted into a computational domain for simulational analysis. Briefly, the steps involved in the fabrication process shown in FIG. 10 include: (a) Spin-coating of photoresist (PR); (b) UV photolithography of the PR; (c) Development of the PR; (d) PDMS casting over developed PR, followed by PDMS curing; and (e) PDMS bonding to a cap (e.g., microscope slides, coverslip, glass, etc.). The devices can be tested visually for structural and fluidic integrity using fluorescent dyes. Fabrication of microfluidic devices from PDMS can be modulated to vary the widths, depths, PDMS concentration and baking time.

Additional methods can be used for preparing the devices, such as the following example. The AutoCAD designs can be printed at high resolution on high-quality chrome masks (spot size of 0.25 μm with a minimum feature resolution of 1 μm. The chrome masks can be used for UV patterning of the desired thickness of positive resist spun on top of a silicon wafer. Silanization via the use of an adhesion promoter (Hexamethyldisilazane, HMDS) can be used to enhance the strength of bonding of the photoresist to the silicon wafer. Sylgard 184 PDMS (Dow Corning, Midland, Mich.) can be poured over developed photoresist to generate complementary microchannels in PDMS. The PDMS can be cured at 60° C. for 4-6 hours in an oven, following which the PDMS can be peeled off from the master. Through holes, defining the inlets and outlets, can be punched using a beveled 25-gauge needle. The bonding surfaces of the PDMS and a pre-cleaned (ultrasonicated) glass slide/wafer can be bonded following oxygen plasma treatment. Tygon Microbore tubing with an outside diameter of 0.03" and inner diameter of 0.01" connected to 25-30 gauge stainless steel needle can be used for world-to-chip interfacing. The completed device can be sterilized by autoclaving at 121° C. for 15 minutes and stored in sterile environment until usage. The finished devices can be tested visually for structural integrity, particularly paying attention to the post structures. The fluidic integrity of the ports and PDMS/glass slide seal can be verified at the operational flow rates.

Various devices configurations can be obtained in accordance with the invention, with central chamber size ranging from 100 μm to 10 mm, surrounded by capillary channels of width 5 μm to 500 μm and height 5 μm to 500 μm, separated by posts 5 μm to 500 μm with gaps of 500 nm to 50 μm. In one example, the device can include of a ~1 mm sized central chamber surrounded by ~20 μm capillary channels with a depth of ~100 μm. Posts separating the chambers can be ~50 μm wide with ~1 μm gaps. The provisional shows an SEM image of two channels joined by ~50 μm long slits fabricated in our laboratory with PDMS using conventional soft lithography techniques. By comparing the yield and performance of different gap sizes in devices, tradeoffs between gap size and performance of wound healing, hemostasis, ischemia, hypoxia, and myocardial infarct can be studied in these devices.

Figure 2:
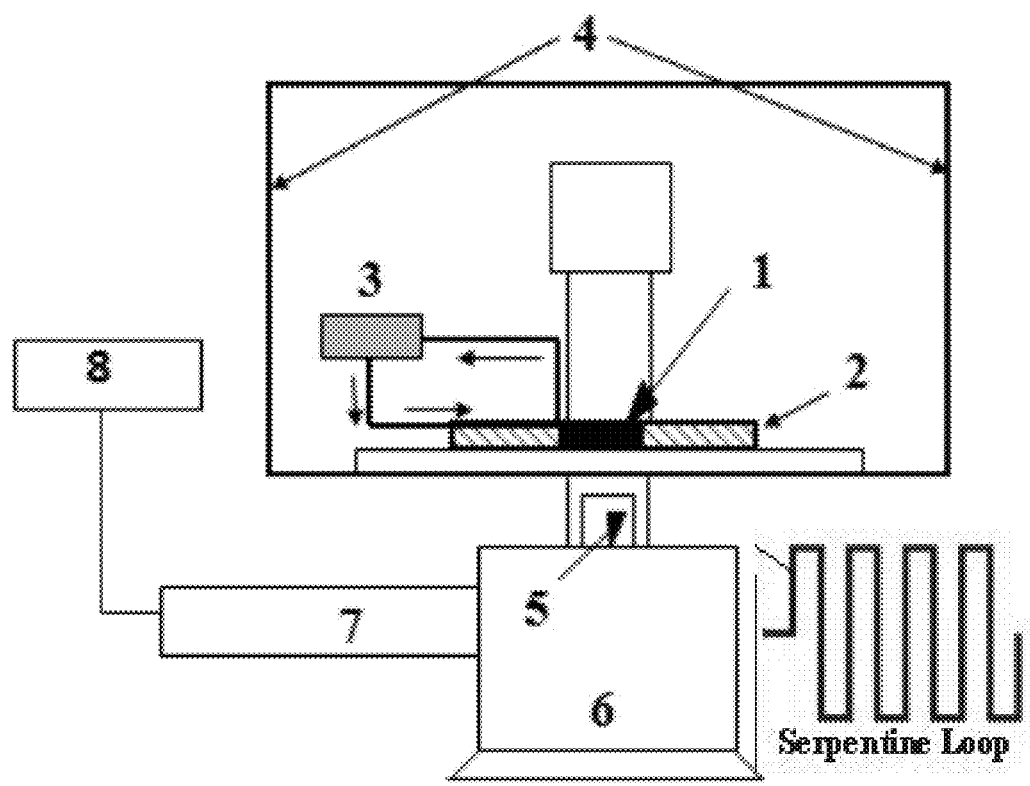
FIG. 2 illustrates a system that can utilize the devices of the invention.

FIG. 2 shows a drawing showing the components of a system used for screening wound healing or hemostasis. The system shows a non-limiting example of a system for performing wound healing or hemostasis drug delivery vehicle screening assays according to the present invention. The system comprises a pumping means (3) such as a peristaltic pump (for recirculation/multiple pass) or a syringe pump (single pass) to move fluids through microfluidic channel networks. For experiments with a peristaltic pump, a microfluidic chip (1) is placed on an automated stage device (2) and connected to a pump (3) that is connected to inlets, outlets, and, optionally, ports on the microfluidic chip (1). The microfluidic chip (1) is preferably contained within an incubation chamber (4) and is positioned over an objective lens (5) of a brightfield, phase contrast or fluorescent microscope (6). Optical means such as a CCD camera or video camera (7) are used to visualize cells within the microfluidic chip (1). The camera (7) is in communication with a computer (8) for data collection and control of microscope (6), camera (7), and the microscope mounted accessories. For experiments with a syringe pump, the syringe pump (3) is connected to the microfluidic chip (1) and fluid leaving the microfluidic chip (1) is sent to waste (not shown).

Wound Healing

In one embodiment, the present invention includes a microfluidic device and assay for studying wound healing phenomena. The microfluidic device can be realistic as shown in FIGS. 1A-1D, or it can be idealized (e.g., with straight or linear channels). The device can be configured to disrupt cell cultures at respective tissue spaces and/or locations in fluid channels. Following disruption, the time and the process taken for the cells to migrate this area is determined (e.g., imaged). This process can provide uniform and repeatable results. Also, the device can be used to create a uniform location devoid of cells and subsequent closing of this location with migrated cells from other locations in the device, where the device can include a 3D matrix to model wound healing. The device allows the creation of a 3D matrix to study wound healing. In addition, uniform and repeatable locations of wound healing can be generated enabling studies for migration of the healing cells into the location.

Figure 3:
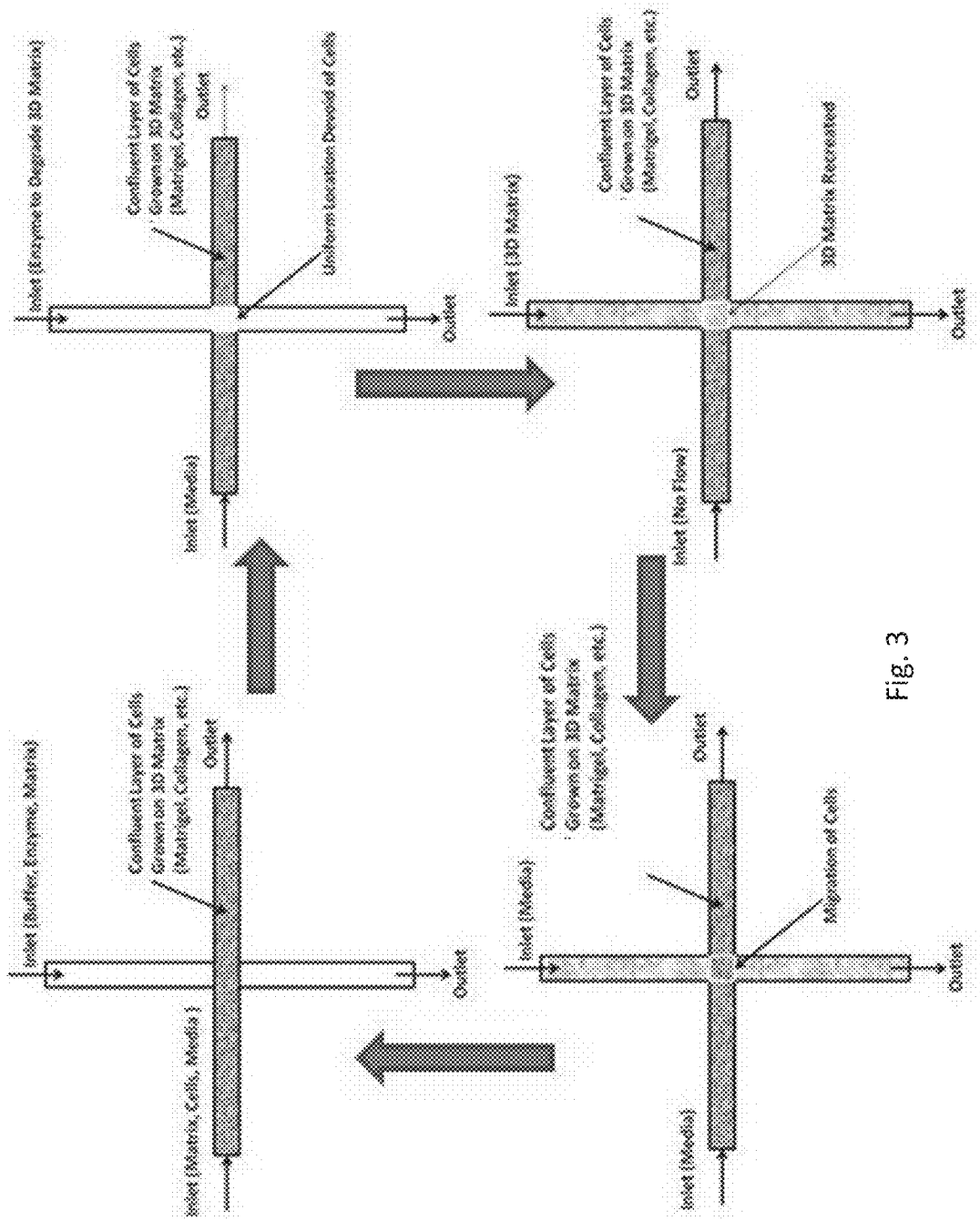
FIG. 3 illustrates a system and method of a device of the invention.

FIG. 3 shows an idealized system with an intersection between two channels, each channel having an inlet and an outlet; however, the methodology can be performed in an SMN. The embodiment in FIG. 3 can be a portion of an IMN or SMN. As shown, the system includes a first inlet configured for introducing matrix, cells, media, or other into a culture channel in the first step, where a confluent layer of cells is grown on a 3D matrix, such as matrigel, collagen, or the like. A second inlet is fluidly coupled with an injury channel, which has an intersection with the culture channel at an angle (e.g., 90 degrees or orthogonal). The second fluid inlet is used for introducing buffer, enzyme, and matrix into the system during the first step. The culture channel and injury channel both have outlets opposite of the inlets on the other side of the junction thereof. Once there is a confluent layer of cells, the second step includes introducing media into the culture channel through the inlet, and introducing an enzyme or other into the injury channel to degrade the cells and/or matrix at the junction between the culture channel and injury channel. As such, step 2 results in a uniform location devoid of cells at the junction. The rest of the culture channel can still have the confluent layer of cells on the 3D matrix. Step 3 includes terminating flow to the culture channel, and introducing 3D matrix material into the injury channel, which results in a 3D matrix being recreated. Step 4 includes introducing media flow into the culture channel and into the injury channel. During step 4, or thereafter, cells can migrate into the junction onto the new 3D matrix. The cell migration can be monitored and analyzed, such with video machine monitoring. Step 2 causes the injury to simulate a wound, and step 4 shows wound healing.

During the experimental protocol, various drugs or therapeutic protocols can be screened to evaluate their effect on (e.g., whether they inhibit or promote) wound healing.

Accordingly, the device and wound simulation protocol can be used in a method for studying cell migration during wound healing in a 3D environment. The device and wound simulation protocol can be used in a method for creating fixed and repeatable size of wound (e.g., devoid of cells). The device and wound simulation protocol can be used in a method for creating wounds with cells on different matrices (e.g., natural, synthetic). The device and wound simulation protocol can be used in method for degrading 3D matrices in a microfluidic device. The device and wound simulation protocol can be used in method for studying effects of therapeutics on wound healing. The device and wound simulation protocol can be used so that the channels can be coated with varying matrices. The device and wound simulation protocol can be used studying wound healing with primary cells and cell lines. The device and wound simulation protocol can be used to study migration of cells (e.g., leukocytes) on wounded cells (e.g., endothelial, fibroblast, etc.). The device and wound simulation protocol can be used to study closure of wounds under varying conditions of 3D matrix. The device and wound simulation protocol can be used to study wound healing under cell culture media, apheresed blood, or whole blood.

In one embodiment, a wound healing test device can include: a first flow channel having an first inlet and a first outlet; a second flow channel having a second inlet and second outlet and a junction with the first flow channel, the junction being between the first inlet, first outlet, second inlet, and second outlet; a 3D matrix coated on an internal surface of the first flow channel between the first inlet and junction and/or between the junction and first outlet, wherein the junction includes the 3D matrix at the junction in a first configuration, is devoid of the 3D matrix at a second configuration, and includes a second 3D matrix in a third configuration.

In one embodiment, the device can include cells growing on the 3D matrix in the first flow channel between the first inlet and junction and/or between the junction and first outlet in the first, second, and third configurations, wherein the junction includes cells growing in the first configuration and is devoid of cells growing in the second configuration.

In one embodiment, the device can include cells migrating into the junction onto the 3D matrix from the first flow channel in the third configuration.

In one embodiment, the device can include a bioactive agent in the junction.

In one embodiment, a method of assaying wound healing can include: providing the device of one of the embodiments; growing cells on the 3D matrix in the first flow channel; and introducing an agent that removes the 3D matrix from the junction; introducing a 3D matrix material into the second flow channel so as to form the second 3D matrix in the second flow channel and junction; and detecting cellular migration into the junction onto the second 3D matrix. In one aspect, the agent that removes the 3D matrix includes an enzyme. In one aspect, the method can include removing cells in the 3D matrix in the junction before introducing the 3D matrix material into the second flow channel. In one aspect, the method can include introducing a bioactive agent into the junction; and determining whether the bioactive agent modulates cellular migration into the junction. In one aspect, the method can include comparing a first matrix material to a different second matrix material for cellular migration into the junction. In one aspect, the cells are primary cells or cell lines.

Hemostasis

In one embodiment, the present invention can include a device and protocol for studying hemostasis. As such, the device and protocol can model a hemorrhage in the device. The device and protocol can be used to screening for hemostatic agents that promote hemostasis. The device and protocol can provide a realistic or ideal in vitro model that is suitable for dynamic assays. The configuration of the device and performance of the protocol can provide results in the in vitro model that are predictive of in vivo efficacy. The device and protocol can be used for quantitative prediction of the efficacy of new hemostatic agents, thereby accelerating their development. The device and protocol can accurately reproduce the variety of physiological (e.g., blood flow, platelet adhesion) and biological (e.g., endothelial response, coagulation pathway) mechanisms involved in the hemostatic response to vascular injury. The device and protocol can be used to monitor formation of a thrombus, and restoration of hemostasis in the presence of a hemostatic agent, which can be observed in real-time. The device and protocol can be used to model clot formation and occlusion after induced injury. The device and protocol can be used to study of parameters including injuries of varying size, dilution, and environmental change induced coagulopathy. In one aspect, large animal (e.g., rabbit, pigs) experiment models can be performed to validate results.

In one embodiment, the device can provide accurate representation of thrombosis and hemostasis, in response to vascular injury, occurring under simulated physiologic conditions. The device can reproduce the morphological size, physiological blood flow and cellular (e.g., biological) make-up of circulatory vessels (see FIGS. 1A-1D). Wound models of varying size (e.g., micron to mm), along with altered mechanical and chemical environments, can be readily created and investigated within this device. The device can be made of a disposable, biocompatible and optically clear plastic with a vascular and tissue side. The vascular channels in the device can be cultured with a confluent layer of endothelial cells to mimic the vascular environment. Tissue spaces adjacent to the vascular wall can be coated with tissue matrix (e.g., collagen, matrigel, etc.). Bleeding wounds of varying sizes can be developed in the device. Candidate hemostatic agents can be flowed in the flow channels of the device at physiologically realistic flow rates, and their ability to restore hemostasis by initiating the coagulation cascade at the wound site can be studied. The device can be used for conventional imaging-based endpoint determinations as well as medium to high-throughput screening or real time visualization with a visualization device. By providing an accurate, quantitative and predictive model of thrombosis and hemostasis, the device can reduce the need for animal experiments and establish a new paradigm in the discovery and development of hemostatic agents.

The device and protocol can be used to model clot formation and occlusion in response to an induced injury. However, the device can be used to study other parameters including vascular injury of varying size, altered coagulation protein concentrations, pH and temperature. Hemostatic dressings can be tested in the device in addition to new hemostatic agents.

The device and protocol can screen a variety of hemostatic agents. However, agents do not work the same way. An ideal hemostatic agent can be: (a) safe to administer, (b) work rapidly and be efficacious, (c) easy to use, (d) affordable, and (e) approved by FDA for use in the US. These agents fall under different classes as shown below.

Physical or Mechanical Agents: Physical agents work by providing either a pressure against the wound such as tourniquets or that polymerize on the wound surface rapidly stopping the bleeding. Common examples are bone wax (e.g., ostene), acrylates (e.g., Dermabond, Tissu-Glu), or the like.

Caustic Agents: This class of hemostatic agents causes some tissue destruction, initiating protein coagulation and precipitation. Common examples are zinc chloride, ferrous subsulfate, silver nitrate, aluminum chloride and mineral zeolite known by the trade name of QuickClot.

Biologic Physical Hemostatic Agents: This group of hemostatic agents mimics biologically found molecules or proteins. As a class, they promote platelet aggregation and coagulation by providing a three-dimensional meshwork for clotting to take place. Key agents in this category include gelatin (e.g., Gelfoam), poly-N-Acetyl Glucosamine (e.g., HemCon), and collagen (e.g., Collastat).

Physiologic Agents: This class of hemostatic agents either provokes a strong physiologic response of vasoconstriction or mimics the later stages of the coagulation cascade. These include thrombin (e.g., Thrombstat), fibrin (e.g., Tisseel), platelet gel (e.g., Vitagel), and recombinant factor VIIa.

The device or portions thereof are shown in FIGS. 4-9. These can be included as idealizes IMN or SMN, such as in FIGS. 1A-1D. The device can be used to predict the efficacy of hemostatic agents in restoring hemostasis. The device can be fabricated using volume friendly lithography methods and fabricated in a low cost optically clear and biocompatible polymer (PDMS) substrate.

Figure 4:
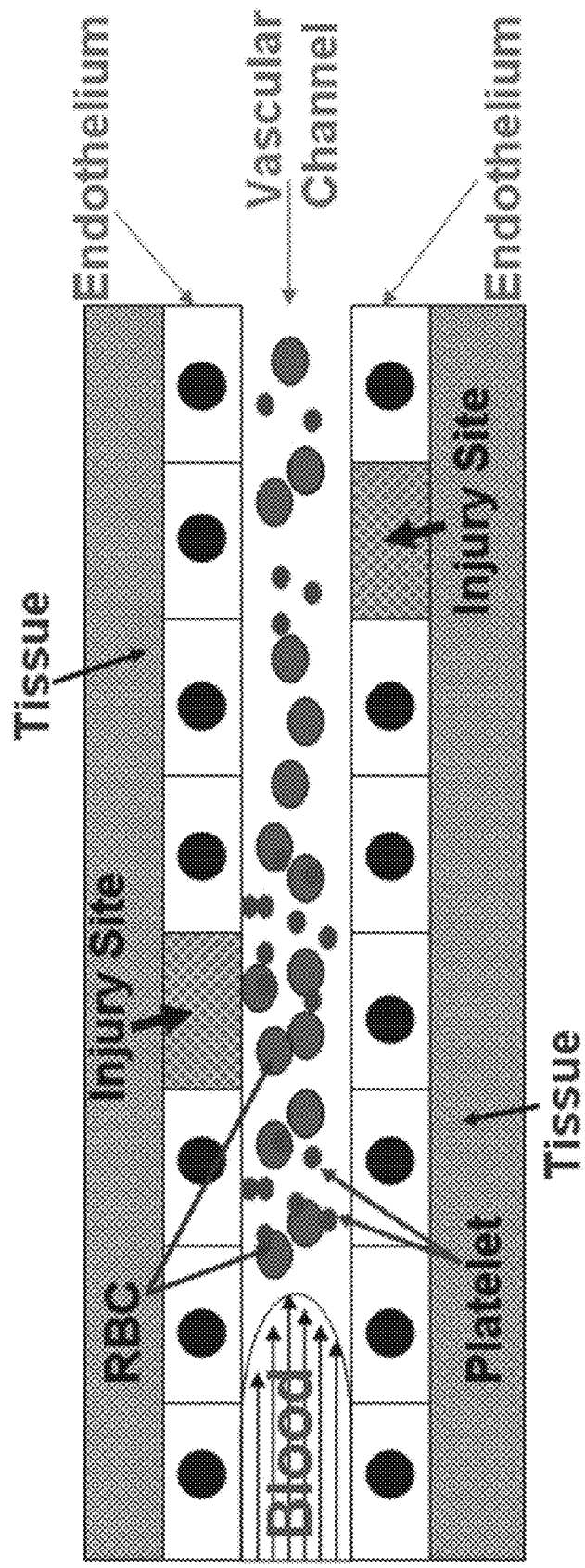
FIG. 4 illustrates a portion of a device of the invention.
Figure 8:
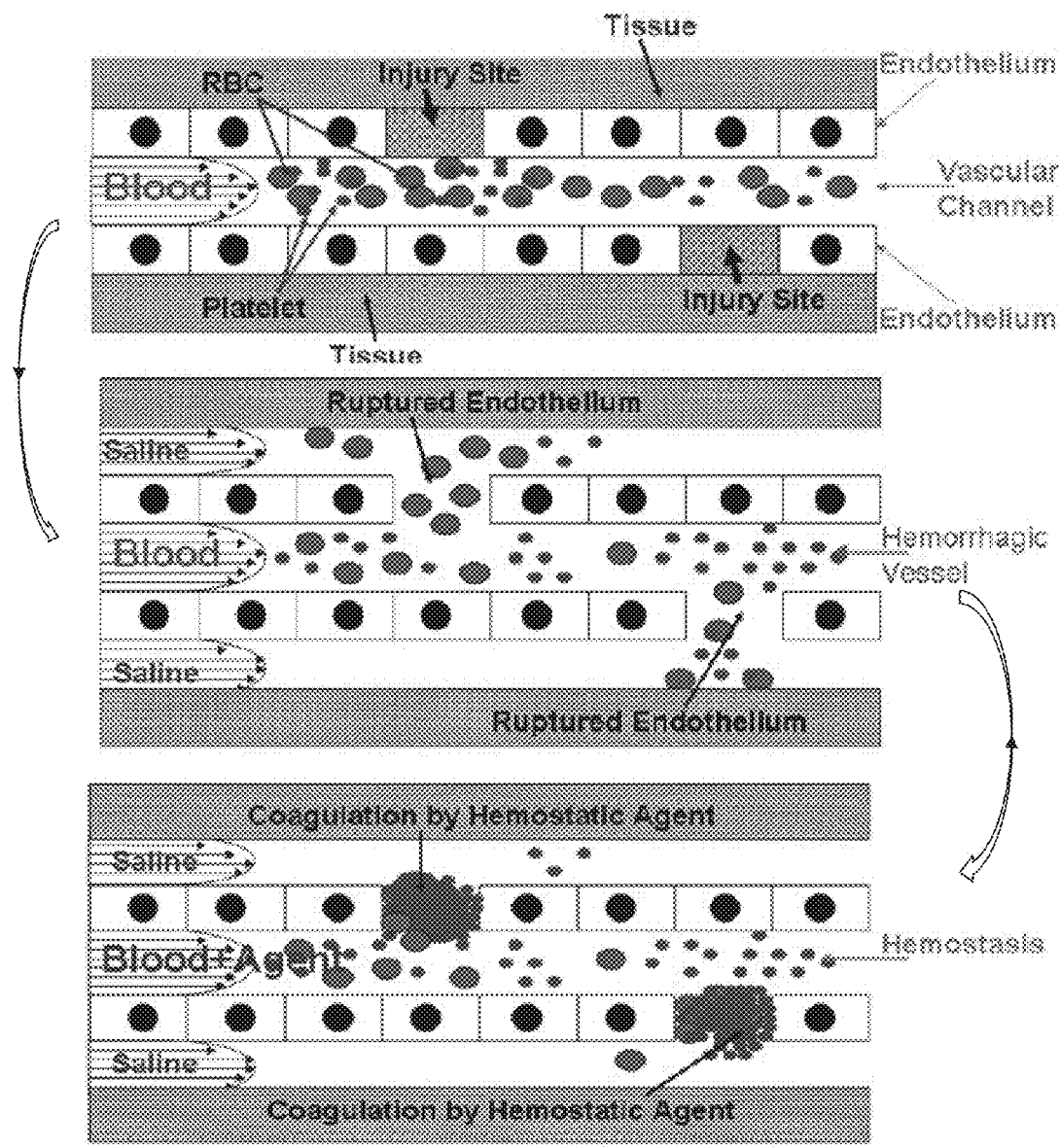
FIG. 8 illustrates a method of performing an assay and corresponding portion of a device of the invention.
Figure 9:
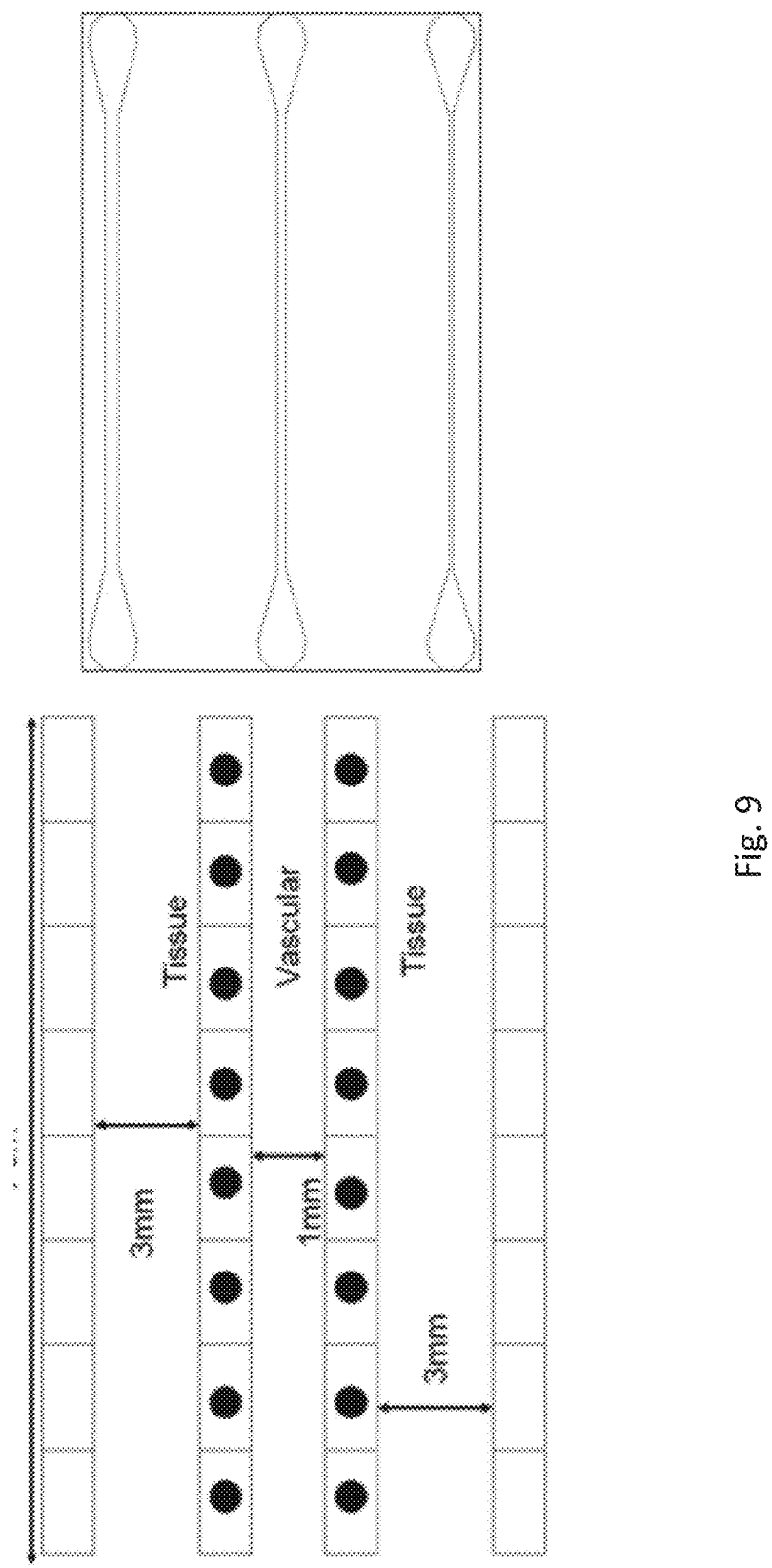
FIG. 9 illustrates a portion of a device of the invention.

FIGS. 4 and 8 show schematics of portions of fluidic pathways with and without tissue spaces of the device. The device can include a vascular channel (e.g., ~1 mm, the size of femoral artery in rabbit) lined with endothelial cells and a parallel channel and/or tissue space where tissue cells, such as smooth muscle cells, can be cultured. Blood or media can be circulated in the vascular channel at representative arterial pressures, thereby reproducing the physiological and cellular vascular environment. Vascular injury of different sizes can be created rapidly in the device to initiate bleeding from the vessel wall of the vascular channel. In addition, other critical wound effects (e.g., dilution, pH change, etc.) can also be represented. Hemostatic agents under study can be injected and their effect on restoring hemostasis by formation of platelet plugs at the injury site can be studied quantitatively.

Accordingly, the device can be used to study biologically relevant varying sizes of vascular injury. The device can be used with physiologically realistic flow accounting for blood transport and vessel pressures. The device provides the ability to study the effects of blood loss leading to: Dilution of coagulation factors; Changes in pH; Changes in temperature; and Metabolic changes. The device provides the ability to gather real-time information, such as through visualization with a visualization device (camera). The in vitro device can be used for predicting the efficacy of hemostatic agents in vivo. The device can be used for simulating restoration of hemostasis (e.g., coagulation at the vascular injury site). The device can be used to culture tissue cells (e.g., smooth muscle, fibroblasts) in addition to vascular cells (e.g., endothelial cells). The device can be used to culture endothelial cells in the vascular channel with a vascular injury (e.g., open wound) site in the vascular channel, and then to study restoration of hemostasis using hemostatic agent to close the wound site. The design of the device can be used in high throughput screening and testing with several hemostatic agents.

The device can include an optically transparent or transmissive plastic body that is disposable with an in vivo realistic microcirculatory network (e.g., 10-100 μm size range) with a complex fluid channel network morphology including branching and loops and a simulated vascular wall with an endothelial layer growing thereon. The device can be a microfluidic chip that mimics in vivo geometries, which can be used to study the wound healing or hemostasis and particle/cell adhesion on the endothelium. The developed chip allows for detailed understanding of differential adhesion of cells in a wound healing or hemostasis environment.

Figure 5:
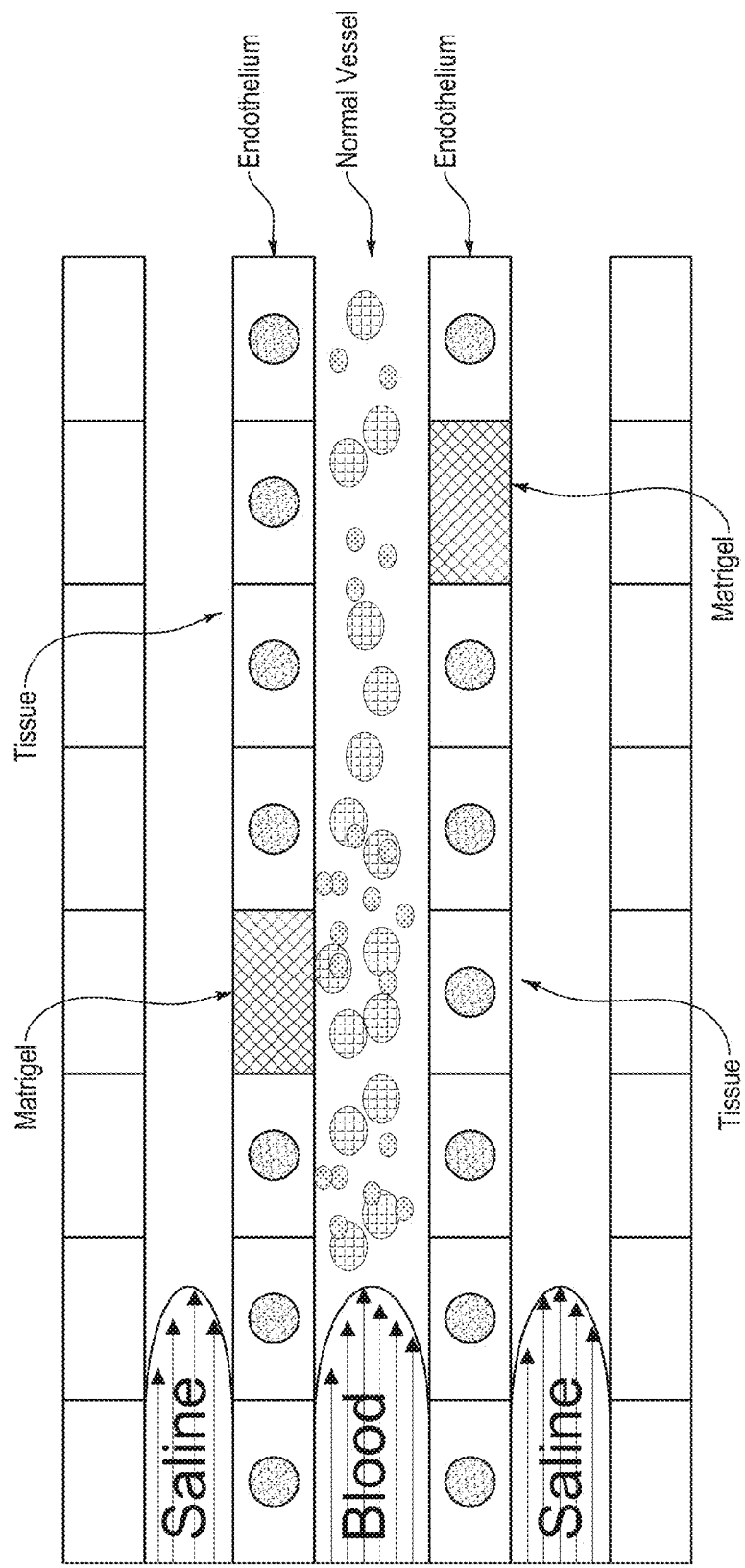
FIG. 5 illustrates a portion of a device of the invention.

The device can include three parallel channels (e.g., idealized or realistic) ranging in size from 100 μm (e.g., for smaller vessels) to 1-5 mm wide (e.g., larger vessels). The central channel of the device can represent the vascular channel while the outer channels represent the tissue area (FIGS. 5-9). The central channel can have predefined gaps (e.g., micron or mm size) to serve as wound mimics. Matrigel (e.g., a degradable ECM component) can be embedded into the gap portions of the vessels to act as temporary barriers to blood flow (FIG. 5). Degradation of the matrigel can result in opening of the wounds/holes and permit blood flow into the side channels. Endothelial cells can be cultured in the central channel to represent the vascular surface. The two outer channels represent the tissue sections.

Figure 6:
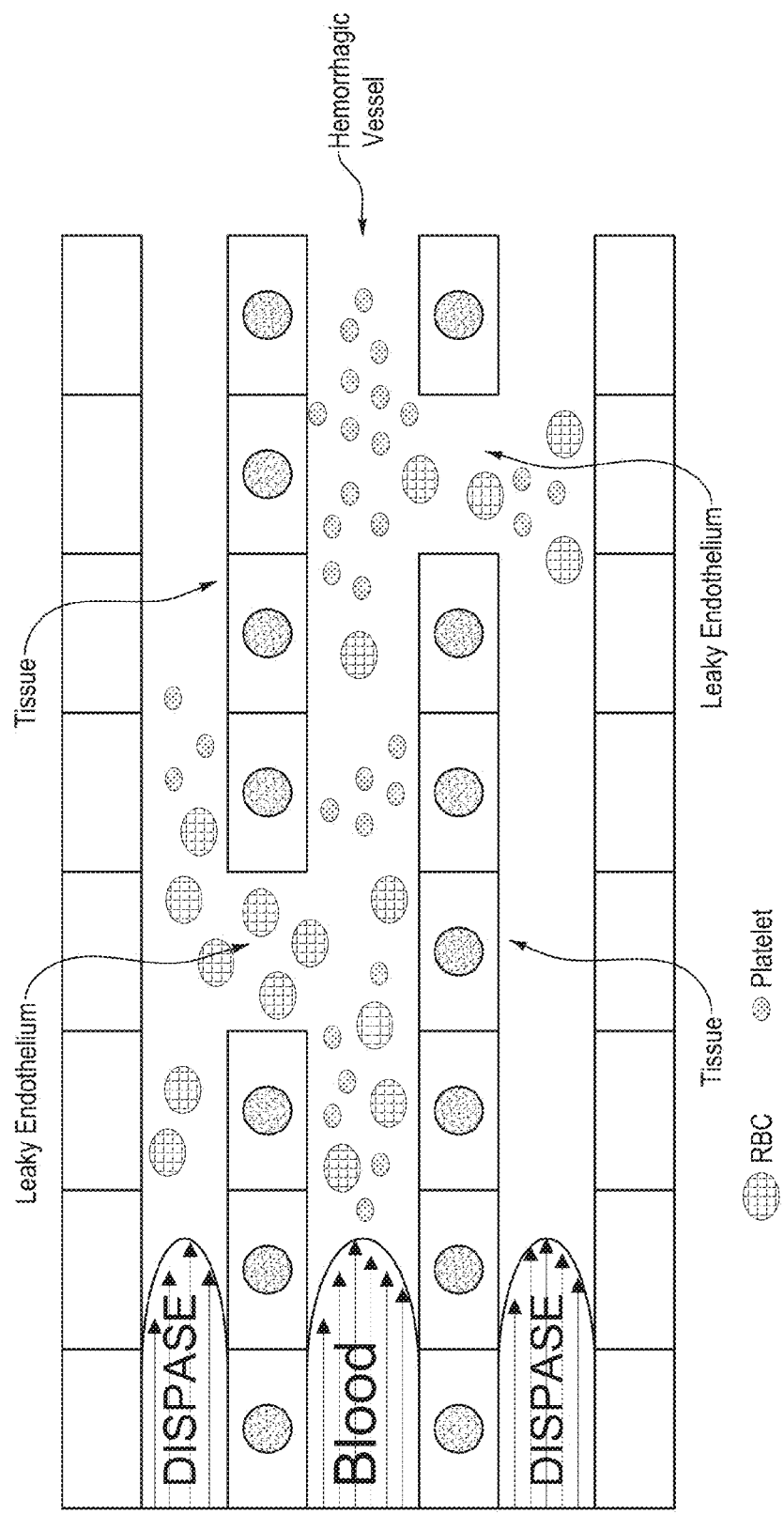
FIG. 6 illustrates a portion of a device of the invention.
Figure 7:
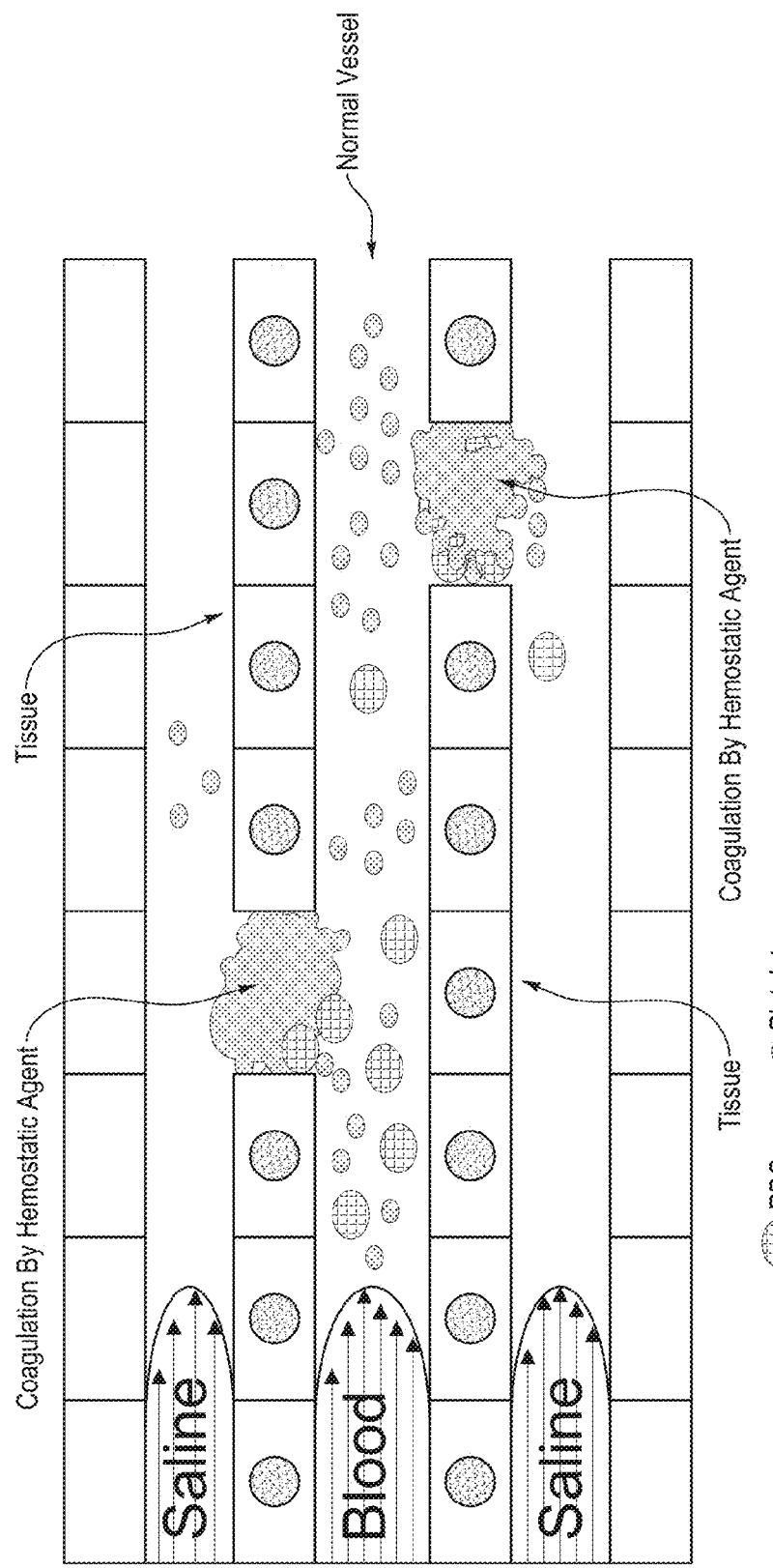
FIG. 7 illustrates a portion of a device of the invention.

Blood comprising of red blood cells (RBCs), platelets, or the like can be pumped/perfused in the central channel with or without drug candidates) using a peristaltic pump and maintained in a circulation loop. Saline solution can be pumped in the outer channels using a peristaltic pump and maintained in a circulation loop. Flow rates can be chosen based on the vessel size and physiologic arterial/venous parameters. Once a uniform flow has been established in the channels, Phosphate buffer saline (PBS) can be replaced by a matrigel dissolving enzyme (e.g., dispase) solution in the outer channels. Following the degradation of the matrigel thereby creating the "wound" or hole in the vasculature (FIGS. 4 and 6), PBS can then be replenished in the outer channels. The holes between the central channel and outer channels simulate wounds and allow the blood to flow into the tissue section of the channel reproducing the scenario of hemorrhagic shock. (FIG. 6). A hemostatic agent can then be introduced into the vascular chamber (e.g., central channel) and allowed to circulate in the channels (e.g., central and outer channels). At regular time points, the channels can be investigated for ability of the hemostatic agent to block the hole by coagulation (FIG. 7). A hemostatic agent can be able to initiate the coagulation pathway at the injury site and thereby reduce/eliminate blood loss from the central channel to the outer channels. Outcomes can include, among others: (a) extent of clot formation (size); (b) rate of clot formation; and (c) measurement of flow/pressure drop through the vascular and side channels.

In one embodiment, the hemostatic microfluidic device can include: Parallel microchannels 50-500 μm in size and based on microcirculatory physiology; Gap structures (e.g., 10-100 μm in size) that separate "tissue space" (e.g., outer channels) from "vascular space" (e.g., central channel); Dissolvable polymers (Matrigel for example) embedded in the gaps; Culture of endothelial cells in vascular space (e.g., central channel);

In one embodiment, a method of assessing hemorrhage in the hemostatic microfluidic device can include: flowing blood with drug candidate in vascular side (e.g., central channel); and performing visual and/or quantitative measurement of clot formation and blood flow from vascular side (e.g., central channel) to the tissue side (e.g., outer channels). The method can include a comparison with positive control using no agents.

In one embodiment, the device dimensions (FIG. 9) can be based on animal models. For example, in the case of rabbit model, the vascular channels developed can be the size ~1 mm width and 1 cm long. The wound size of 1 mm can be created similar to a rabbit femoral artery. The inlet and outlet ports for connecting tubing can be included. The device can be rendered in AutoCAD for fabrication. The device can be fabricated using conventional soft lithography/replica casting techniques. Accordingly, the device provides detailed microvascular network structures obtained from in vivo animal data are patterned onto PDMS (polydimethylsiloxane) to form a plastic, disposable substrate with optical clarity and good gas permeability enabling cell culture applications. This allows us to recreate in vivo simulated environments in vitro, with similar fluidic/shear conditions and topologies. The patterns of these vessels can include plastic tissue sections that have gaps ranging from 1 μm to 15 μm or wound holes of 1 μm to 15 μm that can be covered with extracellular matrices (e.g., Matrigel, Collagen) that dictate permeation from the vascular to the tissue space. Thus, the device can include a wound healing or hemostasis device and assay: In vitro microfluidic wound healing or hemostasis chip with anatomically realistic features based on in vivo microvascular network images and 5-15 μm (e.g., 9 micron) leaky gaps; Automated protocols for real-time visualization of wound healing or hemostasis and drug delivery; and Customized software to analyze experimental data generated on-chip.

In one embodiment, the device can provide improvements in: Integrated wound healing or hemostasis device; Flow and morphologically realistic environment; Quantitative real-time visualization; Ability to screen new wound healing or hemostasis therapeutics; and Reduced reagent/cell use and disposable chips. In one example, a sample reagent savings for the microvascular network in comparison with flow chamber for studying wound healing or hemostasis by monitoring cell migration/attachment is shown in Table 1.

TABLE 1

Typical Savings for a Microvascular Network Compared to a Parallel Plate Flow Chamber.

| Adhesion Device | Reagent Volume (μl) | Number of Particles/ Experiment | Dead Volume Tubing (μl) |
|---|---|---|---|
| Typical Flow Chamber | 50-2000 | 5E+05 | 32.0 |
| Microvascular Network | 1 | 5E+02 | 3.0 |

We have previously developed computational models for study of fluid and particle/cell motion and adhesion in the networks. Computational mesh for the microvascular network can be created by importing network layouts into the mesh generation module of CFD-ACE+ software, a general-purpose Computational Fluid Dynamics (CFD) code based on the Finite Volume Method (FVM). A three-dimensional hybrid mesh comprising of hexahedral and prismatic elements can be generated to investigate flow features e.g., velocities, shear rates, pressure, etc.) and particle and molecular transport e.g., micro- vs. nano-particle distribution, etc.) (see incorporated applications and provisional). These simulation results can facilitate analysis of flux for different cells (platelets, RBCs, WBCs), biomolecules and their adhesion data in the network.

The methods can also compare data with the device with a database of simulations with descriptions of fluidic shear and particle/cell flux conditions in various regions of the networks. These data can be used in the interpretation of results. Internal data has provided an excellent agreement between experimental and simulation results of perfusion in the network. As such, transient perfusion studies comparing experimental and simulation results can be performed with the SMN.

In one embodiment, the device can include: a microfluidic chip with embedded microvascular networks and tissue space to study wound healing or hemostasis; a microfluidic chip with areas defining tissue and vascular space; a microfluidic chip with areas defining tissue and vascular space separated by a porous (1-30 μm) can with multiple gaps in the wall defining the pores; a microfluidic chip with areas defining vascular and tissue space capable of growing various types of cells; a microfluidic chip with areas defining vascular and tissue space capable of growing multiple type of cells in co-culture; a microfluidic chip with areas defining vascular and tissue space capable of growing cells; a microfluidic chip with areas defining vasculature capable of having a vascular matrix; a microfluidic chip with areas defining a tissue space capable of having extracellular matrix or basement membranes (e.g., matrigel, collagen, etc.); a microfluidic chip for use in studying real-time circulation of cells and adhesion of cells, such as cells involved in wound healing or hemostasis; and a microfluidic chip for drug screening. The studies can be quantitative and in real time with visualization with a resolution for single cells. The cells can be in a 3D matrix. The cells can be adherent or suspension cells. The gradients in the SMN can be multi-directional. The device can be used in a fully automated system, such as FIG. 2.

The device can be used to study the effect of loss of blood components (e.g., platelets, RBC) by testing with range of diluted concentrations (10%, 25% and 50%) of whole blood. In addition, varying concentrations (pg/ml to mg/ml) of chemicals (e.g., drugs) and native and synthetic biomolecules (e.g., tissue factor (TF)) can be analyzed.

In one embodiment, a hemostasis device can include: a central channel having an inlet and an outlet; one or more outer channels adjacent to the central channel, each outer channel having an inlet and an outlet; a wall located between the central channel and one or more outer channels; at least one aperture between the central channel and one or more outer channels so as to fluidly couple the central channel and one or more outer channels; and a degradable matrix located in the at least one aperture so as to fluidly isolate the central channel and one or more outer channels from each other.

In one embodiment, the device can include endothelial cells in the central channel and a matrix material in the one or more outer channels.

In one embodiment, the device can include blood, whole or diluted, in the central channel.

In one embodiment, the device can include a hemostatic agent in the central channel or one or more outer channels.

In one embodiment, a method of assaying hemostasis can include: providing the device of one of the embodiments; culturing endothelial cells in the central channel; degrading the degradable matrix in the at least one aperture; flowing blood, whole or diluted, through the central channel; and determining whether or not hemostasis occurs at the at least one aperture. In one aspect, the method can include introducing an agent into the central channel or one or more outer channels; and determining whether or not the agent is a hemostatic agent. In one aspect, the method can include flowing a fluid through the one or more outer channels, the fluid being introduced into the inlet of the one or more outer channels being devoid of blood or diluted blood. In one aspect, the method can include determining clot size induced by the hemostatic agent. In one aspect, the method can include determining rate of clot formation by the hemostatic agent. In one aspect, the method can include measuring flow and/or pressure drop through the central channel and one or more outer channels.

EXPERIMENTAL

Culture of Endothelial Cells in the Vascular Channel:

The methods can include culturing endothelial cells from desired origins in the vascular channels of the device. Success can be defined as the achievement of >90% confluency of endothelial cells. The vascular channel can be coated with fibronectin (50 μg/ml) and allowed to incubate at room temperature for 60 minutes. The channel can then be washed with EBM medium supplemented with EGM SingleQuots and 20% FBS to remove excess fibronectin. The fibronectin-coated device can be kept in an incubator at 37° C., 5% $CO_2$, while endothelial cells in flasks can be prepared for injection. Endothelial cells at a concentration of $5 \times 10^{\wedge}6$ cells/ml can be injected into the network using a syringe pump at a flow rate of 10 μl/min. An inverted microscope can be used to observe cell injection to ensure an even spread of cells throughout the channels. Flow injection can be stopped and the device can be stored in the incubator at 37° C., 5% $CO_2$. Cell media can be changed every day using a syringe pump until the cells are >90% confluence. Propidium iodide staining (which stains cells with compromised membranes) can be used to make sure that the cells grown in the channels are in healthy state.

Hemostatic Agent Assay:

The device can be used for hemostatic agent screening. A hemostatic agent can be used to demonstrate coagulation at the vascular injury site in the device. A placebo agent (e.g., bovine serum albumin) can be used as a control.

Choice of Hemostatic Agent:

Biomolecules such as tissue factor (TF) can be used as a surrogate for hemostatic agents. TF is the primary cellular initiator of blood coagulation via the extrinsic pathway. After vessel injury, the TF:VIIa complex activates the coagulation protease cascade, which leads to fibrin deposition and activation of platelets (see FIGS. 7-8). TF expression by nonvascular cells plays an essential role in hemostasis by activating blood coagulation. In contrast, TF expression by vascular cells induces intravascular thrombosis. The tissue channel (e.g., outer channel) of the device can be coated with TF at a concentration of 1 μg/ml in Hepes-buffered saline/Ca2+ buffer solution by injecting at a flow rate of 10 μl/min. TF can be allowed to adhere to the surface of the channels by incubating at 37° C. and 5% CO2. Saline wash can be initiated to wash off any residual TF.

Activation of TF from Endothelial Cells:

It is known that following injury, endothelial cells are significantly inflamed and start secreting TF. In order to mimic these conditions observed, TNF-α at a concentration of 10 μg/ml can be injected near the wound site of the tissue channel (e.g., outer channel) from the top inlet of the device. It should be noted that endothelial cells cultured in the vascular channel (e.g., central channel) can grow near the wound site opening, and also into the tissue area. Injection of TNF-α can activate the endothelial cells adjacent to the injection site to start expressing TF. At about 8 hour after activation, hemostasis restoration experiments can be initiated.

Hemostasis Restoration:

Whole blood can be kept anticoagulated using corn trypsin inhibitor (CTI). It is known that TF can induce coagulation in presence of CTI as CTI inhibits the intrinsic pathway and does not affect the extrinsic pathway which requires TF for initiation. The blood can be incubated with mepacrine (2 μM) for 30 minutes at 37° C. Mepacrine is a cell membrane permeable fluorescent dye and is received by the dense granules of platelets. This concentration does not alter the biological properties of platelets. Cell media can be replaced in the vascular channel (e.g., central channel) with whole blood, and a perfusion loop can be initiated using a peristaltic pump at varying arterial shear rates (e.g., 15 $sec^{-1}$ to 2000 $sec^{-1}$). A first experiment can be run at high shear rate of 2000 $sec^{-1}$, where the platelets are activated. The whole set up can be placed on the inverted microscope equipped with an incubator to visualize and record the whole process in real-time. Whole blood on contact with TF on the tissue side of the channel can activate the platelets starting the coagulation cascade. The time taken to completely repair (block) the opening can be recorded (FIG. 8). A second experiment can be conducted at a lower shear rate of 500 $sec^{-1}$ where platelets are not activated to compare effects of platelet activation on coagulation.

Two kinds of test tube experiment can be used for comparison studies. In the first experiment, TF can be mixed with whole blood treated with CTI, and coagulation time observed, thereby mimicking a completely mixed situation. In the second experiment, TF can be introduced into the test tube with whole blood mixed with CTI, but the two solutions cannot be mixed. We can let diffusion forces drive the interaction of TF with blood. This scenario mimics diffusional mixing of hemostatic agents with blood in vivo. However, this does not represent the convective transport of blood and diffusional mixing observed in vivo, which is made possible with the device of the invention. Finally, an identical experiment can be performed where instead of coating with TF, BSA can be coated in the tissue channel to characterize the potency of TF as the surrogate hemostatic agent. Coagulation times for all the situations can be compared. It should be noted that other surrogate, natural or synthetic (chemical, biological) agents can be readily tested for potency in the device and assay.

Blood Dilution Assay:

The device can be used to predict the efficacy of hemostatic agents in diluted concentrations of coagulation proteins following fluid restoration. Results obtained can help in future screening of hemostatic agents as effect of dilution can be readily investigated. A potent hemostatic agent should be able to promote coagulation with minimal coagulation proteins.

Heparinized whole blood can be diluted 10%, 25% and 50% respectively using sterile saline solutions to mimic the dilution affects observed following fluid resuscitations. The TF can be coated on the tissue channel (e.g., outer channel) and confluent endothelial cells on the vascular channel (e.g., central channel) can be activated with TNF-α. At the end of 8 hours, diluted blood can be introduced into the vascular channel and the time taken for the clot to form and the ability/inability to completely restore hemostasis can be determined. Data can be compared with the whole blood situation to predict the outcome of blood dilution effects. In addition, test tubes experiments can be performed with a fully mixed and non-mixed TF and diluted blood solutions to compare the coagulation times for standard assays.

Varying Concentrations Assay of Hemostatic Agent (e.g. TF):

Dosage of any drugs can be an important component for successful therapy. Too little or too high concentrations can cause serious consequences for a bleeding situation. The device can provide a platform for assessing the minimal concentrations of hemostatic agents required for coagulation in a fluidic setting. In addition, differences between static and physiological fluid conditions can be studied. Accordingly, the effect of varying concentrations of the TF can be studied. Tissue factor can be coated at a concentration of 10 ng/ml in the tissue channel. Experiments can be repeated as before to assess the coagulation time of the whole blood at the vascular injury site. The time required for clotting can be compared with the baseline case to assess the speed or reduction in the hemostasis restoring process. Test tube experiments can be also be performed. A second experiment with a higher concentration of 10 μg/ml can be conducted to study the extreme dose scenario. 10 ng/ml is not expected to coagulate in less than 5 minutes. 10 μg/ml is expected to coagulate in less than 5 minutes. This can be done with other potential hemostatic agents as well.

One skilled in the art can appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as can be apparent to those skilled in the art. Functionally equivalent methods and apparatuses within the scope of the disclosure, in addition to those enumerated herein, can be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In one embodiment, the present methods can include aspects performed on a computing system. As such, the computing system can include a memory device that has the computer-executable instructions for performing the method. The computer-executable instructions can be part of a computer program product that includes one or more algorithms for performing any of the methods of any of the claims.

In one embodiment, any of the operations, processes, methods, or steps described herein can be implemented as computer-readable instructions stored on a computer-readable medium. The computer-readable instructions can be executed by a processor of a wide range of computing systems.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle can vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It can be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It can be further understood by those within the art that if a specific number of an introduced claim recitation is intended, such an intent can be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art can recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It can be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" can be understood to include the possibilities of "A" or "B" or "A and B."

In addition, where features or aspects of the disclosure are described in terms of Markush groups, those skilled in the art can recognize that the disclosure is also thereby described in terms of any individual member or subgroup of members of the Markush group.

As can be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As can also be understood by one skilled in the art all language such as "up to," "at least," and the like include the number recited and refer to ranges which can be subsequently broken down into subranges as discussed above. Finally, as can be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it can be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

All references recited herein are incorporated herein by specific reference in their entirety.

This patent document incorporates by specific reference in their entirety the following patents and patent applications: U.S. Pat. Nos. 7,725,267; 8,355,876; 8,175,814; 8,380,443; 8,417,465; 8,589,083; U.S. 2010/0227312; PCT/US2013/072081; U.S. 2013/0101991; and U.S. 2013/0149735. These applications provide background and state of the art as well as definitions for terms of art.

This patent document incorporates by specific reference in their entirety co-filed applications that claim priority to the same provisional application U.S. 61/775,158 filed Mar. 8, 2013, which co-filed applications include: U.S. Ser. Nos. 14/202,491; and 14/202,511.

The invention claimed is:

1. A method of assaying cell migration, the method comprising:
 a) providing a device having a first flow channel that intersects a second flow channel at a first junction, the first flow channel having an internal surface that is coated with a first a matrix material;
 b) growing cells on the matrix material in the first flow channel;
 c) injuring and/or removing cells in the junction if cells are in the junction; and
 d) detecting cellular migration of the cells from the first flow channel into the junction.

2. The method of claim 1, wherein the provided device has the matrix material in the junction, the method further comprising:
 removing the matrix material from the junction before the detecting of cellular migration into the junction.

3. The method of claim 2, further comprising:
 a) after the matrix material is removed from the junction, introducing a second matrix material into the junction; and
 b) detecting cellular migration of the cells from the first flow channel onto the second matrix material in the junction.

4. The method of claim 3, further comprising:
 introducing the second matrix material into the second flow channel in order to introduce the second matrix material into the junction.

5. The method of claim 2, wherein the matrix material is removed from the junction by introducing an agent into the junction that removes the matrix material.

6. The method of claim 5, wherein the agent that removes the matrix material includes an enzyme, biomolecule, or chemical.

7. The method of claim 4, further comprising removing cells in the matrix material in the junction before introducing the second matrix material into the second flow channel.

8. The method of claim 1, further comprising:
 introducing a bioactive agent into the junction; and
 determining whether the bioactive agent modulates cellular migration into the junction.

9. The method of claim 4, further comprising:
 a) detecting cellular migration of the cells from the first flow channel into the first junction, wherein the first junction is coated with the first matrix material;
 b) detecting cellular migration of the cells from the first flow channel into the junction having the second matrix material, wherein the first and second matrix materials are different; and
 c) comparing the first matrix material to the second matrix material to determine whether or not the two different matrix materials cause a difference in cellular migration into the junctions.

10. The method of claim 1, wherein the cells are primary cells or cell lines.

11. The method of claim 1, further comprising:
 a) providing a third flow channel that intersects a fourth flow channel at a second junction, the third flow channel having an internal surface that is coated with a second matrix material that is different from the first matrix material in the first junction;
 b) detecting cellular migration of the cells from the first flow channel onto the first matrix material in the first junction; and
 c) detecting cellular migration of the cells from the third flow channel onto the second matrix material in the second junction.

12. The method of claim 11, further comprising comparing the cellular migration onto the first matrix material with the cellular migration onto the second matrix material.

13. The method of claim 1, wherein:
 a) the first flow channel has a first inlet and a first outlet;
 b) the second flow channel has a second inlet and a second outlet and the junction between the first and second channels is between the first outlet and the second inlet; and
 c) the matrix material is coated on an internal surface of the first flow channel between the first inlet and the first junction and/or between the first junction and the first outlet.

14. The method of claim 13, further comprising growing cells on the first matrix material in the first flow channel between the first inlet and the junction and/or between the junction and the first outlet and/or in the junction.

15. The method of claim 13, further comprising:
 a) growing cells on the first matrix material in the first flow channel;
 b) introducing an agent that removes the matrix material and/or cells from the junction;
 c) introducing a second matrix material into the second flow channel and junction so as to form the second matrix material in the second flow channel and junction; and
 d) detecting cellular migration into the junction onto the second matrix material.

16. The method of claim 15, wherein the agent that removes the first or second matrix material includes an enzyme, biomolecule, or chemical.

17. The method of claim 13, further comprising:
 introducing a bioactive agent into the junction; and
 determining whether the bioactive agent modulates cellular migration into the junction.

18. The method of claim 15, further comprising:
comparing celluar migration into the junction on the first matrix material to cellular migration into the junction on the second matrix material.

19. The method of claim 13, wherein the cells are primary cells or cell lines.

* * * * *